United States Patent
Reddy et al.

(10) Patent No.: US 8,481,729 B2
(45) Date of Patent: Jul. 9, 2013

(54) PROCESSES FOR THE PREPARATION OF PALIPERIDONE

(75) Inventors: Manne Satyanarayana Reddy, Hyderabad (IN); Sajja Eswaraiah, Hyderabad (IN); Revu Satyanarayana, East Godavari (IN)

(73) Assignee: MSN Laboratories Limited, Hyderabad, Andhra Pradesh (IN)

( * ) Notice: Subject to any disclaimer, the term of this patent is extended or adjusted under 35 U.S.C. 154(b) by 256 days.

(21) Appl. No.: 12/997,982

(22) PCT Filed: Jun. 15, 2009

(86) PCT No.: PCT/IN2009/000345
§ 371 (c)(1),
(2), (4) Date: Feb. 15, 2011

(87) PCT Pub. No.: WO2010/004578
PCT Pub. Date: Jan. 14, 2010

(65) Prior Publication Data
US 2011/0293889 A1    Dec. 1, 2011

(30) Foreign Application Priority Data

Jun. 16, 2008 (IN) .......................... 1451/CHE/2008
Dec. 29, 2008 (IN) .......................... 3300/CHE/2008

(51) Int. Cl.
*C07D 239/70* (2006.01)

(52) U.S. Cl.
USPC ....................................................... 544/282

(58) Field of Classification Search
None
See application file for complete search history.

(56) References Cited

U.S. PATENT DOCUMENTS

| | | |
|---|---|---|
| 4,804,663 A | 2/1989 | Kennis et al. |
| 5,158,952 A | 10/1992 | Janssen et al. |
| 5,688,799 A | 11/1997 | Vandenberk et al. |

FOREIGN PATENT DOCUMENTS

| | | |
|---|---|---|
| EP | 0 196 132 B1 | 10/1986 |
| EP | 0 368 388 B1 | 5/1990 |
| WO | WO 2008/021345 | 2/2008 |
| WO | WO 2008/024415 A2 | 2/2008 |

OTHER PUBLICATIONS

Written Opinion of the International Searching Authority for International Application No. PCT/IN2009/000345 dated Apr. 20, 2010, "Novel and Improved Processes for the Preparation of Paliperidone".
Notification Concerning Transmittal of International Preliminary Report on Patentability for International Application No. PCT/IN2009/000345 dated Dec. 29, 2010, "Novel and Improved Processes for the Preparation of Paliperidone".
International Search Report from counterpart International Application No. PCT/IN2009/000345, dated Apr. 20, 2010.

*Primary Examiner* — Jeffrey Murray
(74) *Attorney, Agent, or Firm* — Hamilton, Brook, Smith & Reynolds, P.C.

(57) ABSTRACT

The present invention relates to a novel process for the preparation of paliperidone and its intermediates and also relates to an improved process for the preparation of paliperidone compound of formula (I).

(I)

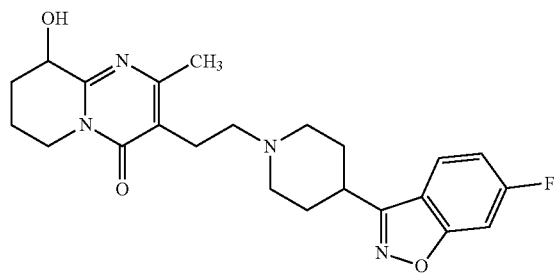

10 Claims, 3 Drawing Sheets

PROCESSES FOR THE PREPARATION OF PALIPERIDONE

RELATED APPLICATION

This application is the U.S. National Stage of International Application No. PCT/IN2009/000345, filed Jun. 15, 2009, which designates the U.S., published in English, and claims priority under 35 U.S.C. §§119 or 365(c) to IN Application Nos. 1451/CHE/2008, filed on Jun. 16, 2008 and 3300/CHE/2008 filed on Dec. 29, 2008, which are incorporated herein by reference.

FIELD OF THE INVENTION

The present invention relates to a novel process for the preparation of paliperidone and its intermediates. Paliperidone is chemically known as (±) 3-[2-[4-(6-fluoro-1,2-benzisoxazol-3-yl)piperidin-1-yl]ethyl]-6,7,8,9-tetrahydro-9-hydroxy-2-methyl-4H-pyrido-[1,2-a]pyrimidin-4-one, which is represented by formula-1. It also relates to an improved process for the preparation of paliperidone.

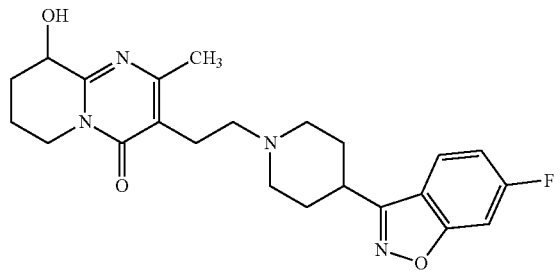

Formula-1

Paliperidone is an active metabolite of risperidone, widely prescribed antipsychotic drug used for the treatment of schizophrenia and bipolar disorder. Paliperidone marketed under the name Invega® acts as a dual antagonist of dopamine D2 receptors in the mesolimbic pathway and 5-$HT_{2A}$ receptors in the prefrontal cortex. Its ability to bind to these receptors in corresponds with its antipsychotic effect and stabilization of some of the antisocial behaviors in patients with schizophrenia. It has been approved in the United States for the treatment of schizophrenia.

BACKGROUND OF THE INVENTION

Paliperidone is an active metabolite of risperidone. Risperidone is metabolized by cytochrome P-450 IID6 to produce 9-hydroxy-risperidone also known as paliperidone. EP 196132 B1 and U.S. Pat. No. 4,804,663 describe certain 1,2-benzisoxazol-3-yl derivatives having psychotic and anti-serotonin activity including 3-[2-[4-(6-fluoro-1,2-benzisoxazol-3-yl)piperidin-1-yl]ethyl]-6,7,8,9-tetrahydro-2-methyl-4,1-pyrido-[1,2-a]pyrimidin-4-one (Risperidone) which is a mixed 5-$HT_2$/D2-receptor antagonist and a typical neuroleptic drug. They exemplify the process for the preparation of risperidone, which includes the condensation of 3-(2-chloroethyl)-6,7,8,9-tetrahydro-2-methyl-4H-pyrido[1,2-a]pyrimidin-4-one mono hydrochloride and 6-fluoro-3-(4-piperidinyl)-1,2-benzisoxazole in presence of N,N-dimethylformamide, sodium carbonate and catalytic amount of potassium iodide. The crude risperidone was crystallized from a mixture of DMF and isopropanol. 9-hydroxyrisperidone, its enantiomeric forms and the $C_{2-20}$ alkanoic acid esters thereof are described in EP 0,368,388. Said esters are considered to be potentially valuable prodrugs of paliperidone.

Risperidone is a highly potent drug having a relatively narrow therapeutic index. It may produce undesirable side effects on over dosage most notably extrapyramidal side effects such as tardive dyskinesia. The most frequently observed adverse reactions include orthostatic hypotension and dizziness, drowsiness, palpitations, weight gain, erectile dysfunction, and a significant increase in rashes and rhinitis.

Accordingly, an antipsychotic agent having the efficacy of risperidone, but causing fewer side effects, would be desirable. It would be desirable to find a compound that has the advantages of risperidone while providing a more predictable dosage regimen in the patient population and decreasing the chances for drug-drug interactions.

Paliperidone was found to overcome some of the problems associated with risperidone. It possesses a longer elimination half life. It has a potent activity in the treatment of psychotic disorders and other conditions, including those that would benefit from an anti diarrheal, an inhibitor of gastro-esophageal reflux and/or an anti emetic, especially in cancer patients receiving chemotherapy and radiation. It is also used in combating autism, hypertension, vascular disorders, obesity, and the withdrawal symptoms associated with cessation of drinking and smoking. It provides a more predictable dosage regimen in the patient population and decreases the chances of drug-drug interactions by avoiding oxidative metabolism for which the cytochrome P4502D6 enzyme system is required.

A process for the synthesis of paliperidone is described in U.S. Pat. No. 5,158,952 according to scheme-1. The preparation of paliperidone via the intermediate 3-(2-chloroethyl)-6,7,8,9-tetrahydro-9-hydroxy-2-methyl-4H-pyrido[1,2-a]pyrimidin-4-one is depicted in the last step of the scheme.

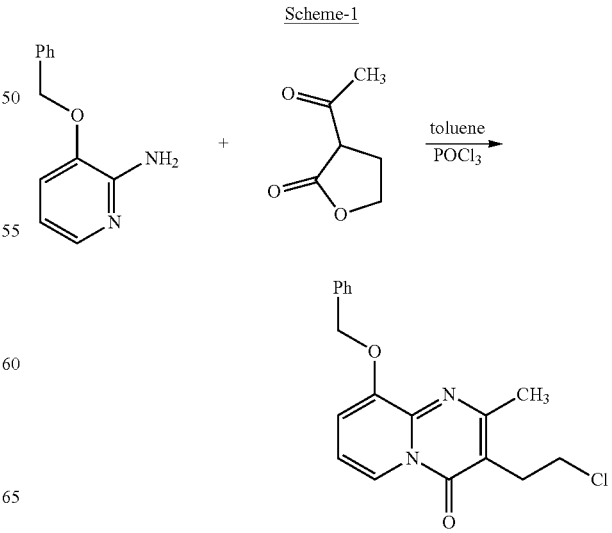

Scheme-1

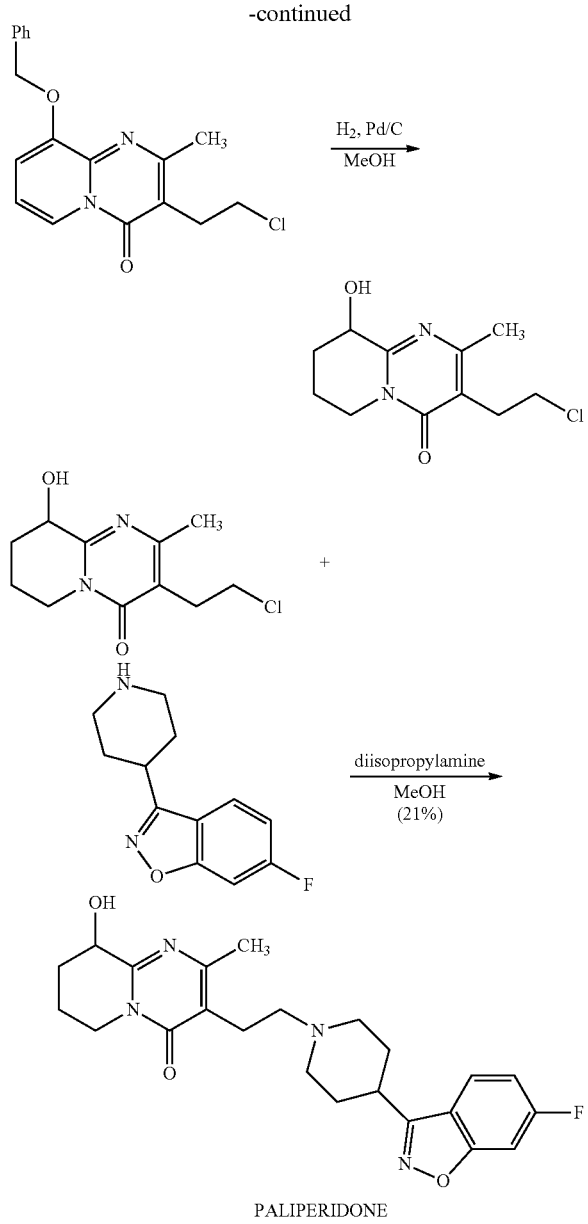

PALIPERIDONE

A process for the synthesis of intermediate 3-(2-chloroethyl)-6,7,8,9-tetrahydro-9-hydroxy-2-methyl-4H-pyrido[1,2-a]pyrimidin-4-one is also described in U.S. Pat. No. 5,688,799. The processes described in the above publications are lengthy, time consuming and result in low chemical yields, making their application in the industry very difficult.

BRIEF DESCRIPTION OF THE INVENTION

The first embodiment of the present invention encompasses an improved process for the preparation of paliperidone, chemically known as 3-[2-[4-(6-fluoro-1,2-benzisoxazol-3-yl)piperidin-1-yl]ethyl]-6,7,8,9-tetrahydro-9-hydroxy-2-methyl-4H-pyrido[1,2-a]pyrimidin-4-one, which is represented by formula-1.

The process comprises the following steps;
a) Reacting 3-benzyloxy-2-aminopyridine, compound of formula-2 with 3-acetyldihydrofuran-2(3H)-2-one, compound of formula-3 in presence of phosphorous oxychloride in toluene to obtain a condensed compound of formula-4, which on in-situ treatment with an acid, leads to deprotection of the benzyl group to provide 3-(2-chloroethyl)-9-hydroxy-2-methyl-4H-pyrido-[1,2-a]pyrimidin-4-one, which is converted into hydrochloride salt, compound of formula-5,
b) in-situ reduction of 3-(2-chloroethyl)-9-hydroxy-2-methyl-4H-pyrido-[1,2-a]pyrimidin-4-one hydrochloride, compound of formula-5 by hydrogenation in the presence of palladium catalyst in acidic conditions to obtain 3-(2-chloroethyl)-9-hydroxy-2-methyl-6,7,8,9-tetrahydro-4H-pyrido[1,2-a]pyrimidin-4-one compound of formula-7,
c) treating 6-fluoro-3-(4-piperidinyl)-1,2-benzisoxazole monohydrochloride, compound of formula-6 with sodium carbonate, followed by condensation with compound of formula-7, in presence of diisopropylethylamine in alcohol solvent to obtain paliperidone,
d) purifying the crude paliperidone formed in step-c, by treating it with an acid followed by a base to provide pure paliperidone compound of formula-1.

The second aspect of the present invention encompasses an improved process for the preparation of paliperidone, comprising the following steps;
a) Reacting 3-(2-chloroethyl)-9-hydroxy-2-methyl-6,7,8,9-tetrahydro-4H-pyrido-[1,2-a]pyrimidin-4-one, compound of formula-7 with 6-fluoro-3-(4-piperidinyl)-1,2-benzisoxazole, crystalline solid compound of formula-8 in presence of diisopropyl ethylamine in alcohol solvent to provide 3-[2-[4-(6-fluoro-1,2-benzisoxazol-3-yl)piperidin-1-yl]ethyl]-9-hydroxy-2-methyl-6,7,8,9-tetrahydro-4H-pyrido-[1,2-a]pyrimidin-4-one (paliperidone),
b) treating the paliperidone obtained in step a) with sodium borohydride, to convert any amount of the 3-[2-[4-(6-fluoro-1,2-benzisoxazol-3-yl)piperidin-1-yl]ethyl]-9-oxo-2-methyl-6,7,8,9-tetrahydro-4,1-pyrido-[1,2-a]pyrimidin-4-one compound of formula-10, formed and present as an impurity, into 3-[2-[4-(6-fluoro-1,2-benzisoxazol-3-yl)piperidin-1-yl]ethyl]-9-hydroxy-2-methyl-6,7,8,9-tetrahydro-4H-pyrido-[1,2-a]pyrimidin-4-one, compound of formula-1,
c) purifying the crude paliperidone formed in step-b, by treating it with an acid followed by a base to provide pure paliperidone compound of formula-1.

The third aspect of the present invention encompasses a novel process for the preparation of paliperidone compound of formula-1, which comprises of the following steps;
a) Reacting 3-(2-chloroethyl)-9-oxo-2-methyl-6,7,8,9-tetrahydro-4H-pyrido-[1,2-a]pyrimidin-4-one, compound of formula-9 with 6-fluoro-3-(4-piperidinyl)-1,2-benzisoxazole, crystalline solid compound of formula-8, in presence of a base in a suitable solvent, to provide 3-[2-[4-(6-fluoro-1,2-benzisoxazol-3-yl)piperidin-1-yl]ethyl]-9-oxo-2-methyl-6,7,8,9-tetrahydro-4H-pyrido-[1,2-a]pyrimidin-4-one, compound of formula-10,
b) treating the compound of formula-10 obtained in step a) with suitable reducing agent to obtain paliperidone,
c) purifying the crude paliperidone formed in step-b) by crystallizing it from alcohol, followed by treatment with acid, washing the aqueous layer with a suitable solvent and subsequent treatment with a base in presence of an alcohol to obtain pure paliperidone compound of formula-1.

The fourth embodiment of the present invention encompasses a novel process for the preparation of paliperidone which comprises the following steps;
a) Reacting 3-(2-chloroethyl)-9-hydroxy-2-methyl-4H-pyrido-[1,2-a]pyrimidin-4-one hydrochloride compound of formula-5 with 6-fluoro-3-(4-piperidinyl)-1,2-benzisoxazole monohydrochloride, compound of formula-6 in presence of a base in suitable solvent, to provide 3-[2-[4-(6-fluoro-1,2-benzisoxazol-3-yl)piperidin-1-yl]ethyl]-9-hydroxy-2-methyl-4H-pyrido-[1,2-a]pyrimidin-4-one, compound of formula-11,
b) reducing compound of formula-11 by using a suitable reducing agent to obtain paliperidone,
c) purifying the crude paliperidone formed in step-b by crystallizing from isopropyl alcohol to obtain pure paliperidone.

The fifth aspect of the present invention encompasses a process for the preparation of crystalline 6-fluoro-3-(4-piperidinyl)-1,2-benzisoxazole, compound of formula-8, which comprises of the following steps;
a) Treating 6-fluoro-3-(4-piperidinyl)-1,2-benzisoxazole monohydrochloride, compound of formula-6, with an aqueous base to convert it into its free base,
b) isolating the obtained solid from water or extracting the free base, compound of formula-8 from the reaction mixture, with a suitable solvent and concentrating the solvent to provide a crystalline solid compound of formula-8.

The sixth aspect of the present invention encompasses a crystalline form of 6-fluoro-3-(4-piperidinyl)-1,2-benzisoxazole

DETAILED DESCRIPTION OF THE INVENTION

Figure 1A:
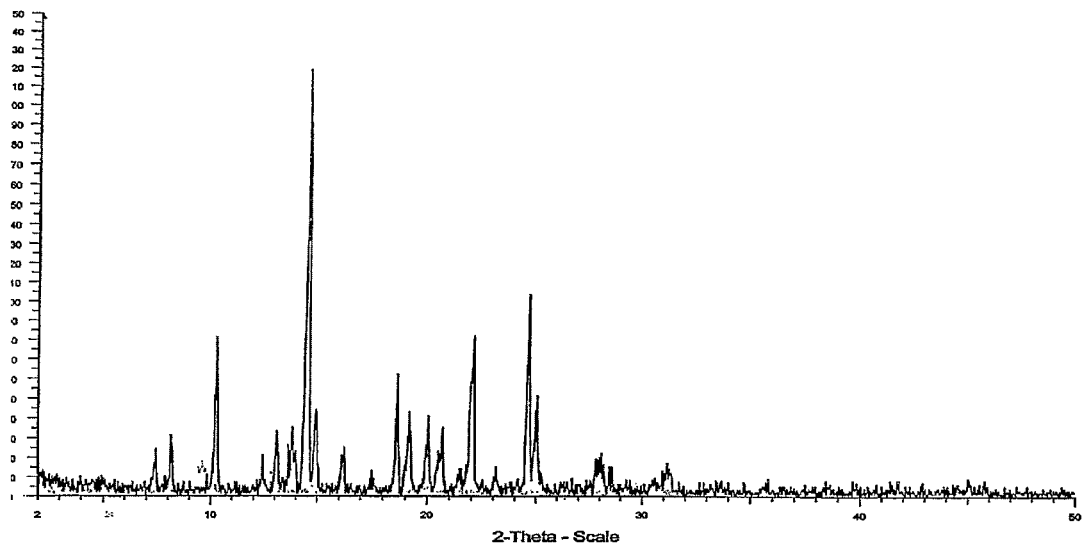
FIG. 1a: Illustrates the powder X-ray diffraction pattern of crystalline (prior art crystalline form-I) paliperidone.
Figure 1B:
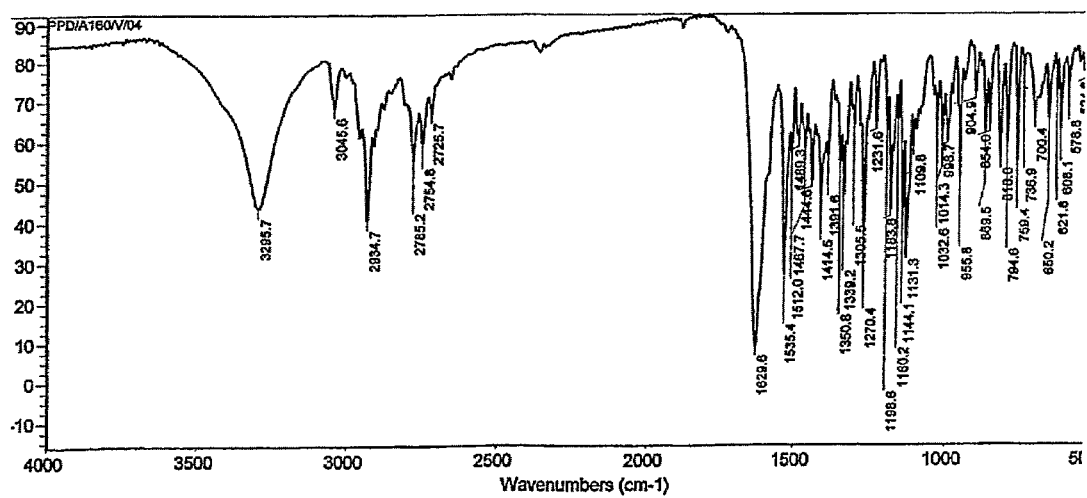
FIG. 1b: illustrates the IR spectrum of crystalline paliperidone.

Unless otherwise indicated, this disclosure uses definitions provided below. As used herein, the term "phase transfer catalyst" refers to catalyst which is selected from the group consisting of but not limited to tetra butyl ammonium bromide, tetra propyl ammonium bromide, tributyl benzyl ammonium bromide, tetra octyl ammonium bromide, tetra butyl ammonium iodide, tetra butyl ammonium hydrogen sulfate, benzyl trimethyl ammonium chloride, benzyl triethyl ammonium chloride, tetra butyl ammonium acetate, tetra butyl ammonium iodide, ethyl triphenyl phosphonium bromide, more preferably tetra butyl ammonium bromide or alkali iodides like sodium iodide, potassium iodide and lithium iodide.

As used herein, the term "inorganic base" refers to a base selected from a group which includes but is not limited to hydroxides of alkali and alkaline earth metals such as lithium hydroxide, sodium hydroxide, potassium hydroxide and the like; carbonates of alkali metals such as sodium carbonate, potassium carbonate and the like and bicarbonates of alkali metals such as sodium bicarbonate, potassium bicarbonate and the like.

As used herein, the term "organic base" refers to a base selected from a group which includes but is not limited to triethyl amine, tributyl amine, diisopropylethylamine N-(1-methylethyl)-2-propanamine, 4-ethylmorpholine, 4-dimethylaminopyridine, 1,8-di-1-azabicyclo[5.4.0]undec-7-ene, 1,4-diazabicyclo[2.2.2]octane, 4-dimethylaminopyridine, pyridine and the like.

As used herein, the term "solvent" refers to water, aliphatic hydrocarbons like hexane, cyclohexane, petroleum ether; or aromatic hydrocarbons like xylene, toluene; or halogenated hydrocarbons like dichloromethane, chloroform, 1,2-dichloroethane; or ethers like diethyl ether, diisopropyl ether, tetrahydrofuran, dimethoxy ethane; or ketones like acetone, methyl ethyl ketone, diethyl ketone, methyl isobutyl ketone; or acetates like ethyl acetate, propyl acetate, butyl acetate; alcohol like methanol, ethanol,1-propanol, isopropyl alcohol, n-butanol; or nitriles like acetonitrile and propionitrile and the like.

As used herein, the term "acid" refers to organic acid which is selected from formic acid, acetic acid, propionic acid and the like or an inorganic acid like hydrochloric acid, hydrobromic acid and sulfuric acid.

As used herein, the term "reducing agent" refers to sodium borohydride, sodium cyanoborohydride, diborane, and hydrogen in presence of a catalyst which include, without limitation heterogeneous catalysts containing from about 0.1% to about 20% by weight of transition metals such as Ni, Pd, Pt, Rh, Re, Ru and Ir, including oxides and combination thereof, which are typically supported on various materials including $Al_2O_3$, C, $CaCO_3$, $SrCO_3$, $BaSO_4$, MgO, $SiO_2$, $TiO_2$, $ZrO_2$ and the like. Many of these metals including Pd may be doped with an amine, sulfide or a second metal such as Pb, Cu and Zn. Useful catalysts include raney nickel, palladium catalyst such as Pd/C, Pd/$SrCO_3$, Pd/$Al_2O_3$, Pd/MgO, Pd/$CaCO_3$, Pd/$BaSO_4$, PdO, Pd Black, $PdCl_2$ and the like. Other useful catalysts Rh/C, Ru/C, Re/C, $PtO_2$, Rh/C, $RuO_2$. The reaction is typically carried out in the presence of one or more solvents including without limitation water, alcohols, ethers, ester, ketones, acids and hydrocarbon solvents such as, methanol, ethanol, isopropyl alcohol, tetrahydrofuran, ethyl acetate, acetic acid, dichloromethane and the like.

The first embodiment of the present invention encompasses an improved process for, the preparation of paliperidone, chemically known as 3-[2-[4-(6-fluoro-1,2-benzisoxazol-3-yl)piperidin-1-yl]ethyl]-6,7,8,9-tetrahydro-9-hydroxy-2-methyl-4H-pyrido[1,2-a]pyrimidin-4-one, which is represented by formula-1. The process comprises the following steps;
a) Reacting 3-benzyloxy-2-aminopyridine, compound of formula-2 with 3-acetyl dihydrofuran-2(3H)-2-one, compound of formula-3 in presence phosphorous oxychloride in toluene to obtain a condensed compound of formula-4, which on treatment in-situ with an acid, leads to deprotection of the benzyl group to provide 3-(2-chloroethyl)-9-hydroxy-2-methyl-4H-pyrido-[1,2-a]pyrimidin-4-one, which is converted into hydrochloride salt, compound of formula-5,
b) in-situ reduction of 3-(2-chloroethyl)-9-hydroxy-2-methyl-4H-pyrido-[1,2-a]pyrimidin-4-one hydrochloride, compound of formula-5 by hydrogenation in the presence of palladium catalyst in acidic conditions to obtain 3-(2-chloroethyl)-9-hydroxy-2-methyl-6,7,8,9-tetrahydro-4H-pyrido[1,2-a]pyrimidin-4-one compound of formula-7,
c) treating 6-fluoro-3-(4-piperidinyl)-1,2-benzisoxazole monohydrochloride, compound of formula-6 with sodium carbonate, followed by condensation with compound of formula-7, in presence of diisopropylethylamine in methanol to obtain paliperidone, d) purifying the crude paliperidone formed in step-c, by suspending it in dichloromethane and treating it with aqueous acetic acid, separating the dichloromethane layer, washing it with methyl isobutyl ketone, treating it with hydrose, followed by basifying with ammonia to provide pure paliperidone compound of formula-1.

In step-a, the deprotection of the benzyl group is carried out by using an acid. In the preferred embodiment of the invention the acid used is hydrochloric acid. The 3-(2-chloroethyl)-9-hydroxy-2-methyl-4H-pyrido-[1,2-a]pyrimidin-4-one formed is obtained as its hydrochloride salt compound of formula-5, which is substantially of high purity which can be isolated or converted in situ into compound of formula-7 of high purity. When crystalline compound of formula-5 or formula-7 are used as inputs in the subsequent reactions, they would enhance the yields of the products formed.

In the U.S. Pat. No. 5,158,952 also exemplifies the above condensation but it is carried out using 6-fluoro-3-(4-piperidinyl)-1,2-benzisoxazole monohydrochloride. The yields reported are poor i.e. around 21%, which were confirmed when these reactions were repeated in the laboratory. When the reactions were carried out using 6-fluoro-3-(4-piperidinyl)-1,2-benzisoxazole free base, compound of formula-8 which is a pure crystalline solid, the yields improved substantially to 80-85%. Also the purity of the product was enhanced to provide paliperidone of >99.5% purity when measured using HPLC.

The present aspect of the invention is represented in Scheme-2.

The second aspect of the present invention encompasses an improved process for the preparation of paliperidone, comprising the following steps;

a) Reacting 3-(2-chloroethyl)-9-hydroxy-2-methyl-6,7,8,9-tetrahydro-4H-pyrido-[1,2-a]pyrimidin-4-one, compound of formula-7 with 6-fluoro-3-(4-piperidinyl)-1,2-benzisoxazole, crystalline solid compound of formula-8 in presence of diisopropyl ethylamine in alcohol solvent, to provide 3-[2-[4-(6-fluoro-1,2-benzisoxazol-3-yl)piperidin-1-yl]ethyl]-9-hydroxy-2-methyl-6,7,8,9-tetrahydro-4H-pyrido-[1,2-a]pyrimidin-4-one (paliperidone), b) treating the paliperidone obtained in step a) with sodium borohydride, to convert any amount of the 3-[2-[4-(6-fluoro-1,2-benzisoxazol-3-yl)piperidin-1-yl]ethyl]-9-oxo-2-methyl-6,7,8,9-tetrahydro-4H-pyrido-[1,2-a]pyrimidin-4-one compound of formula-10, formed and present as an impurity, into 3-[2-[4-(6-fluoro-1,2-benzisoxazol-3-yl)piperidin-1-yl]ethyl]-9-hydroxy-2-methyl-6,7,8,9-tetrahydro-4H-pyrido-[1,2-a]-pyrimidin-4-one, compound of formula-1, c) purifying the crude paliperidone obtained in step-b, by suspending it in dichloromethane and treating it with aqueous acetic acid, separating the dichloromethane layer, washing it methyl isobutyl ketone, treating it with hydrose, followed by basifying it with ammonia to provide pure paliperidone compound of formula-1.

The present aspect of the invention is represented in Scheme-2.

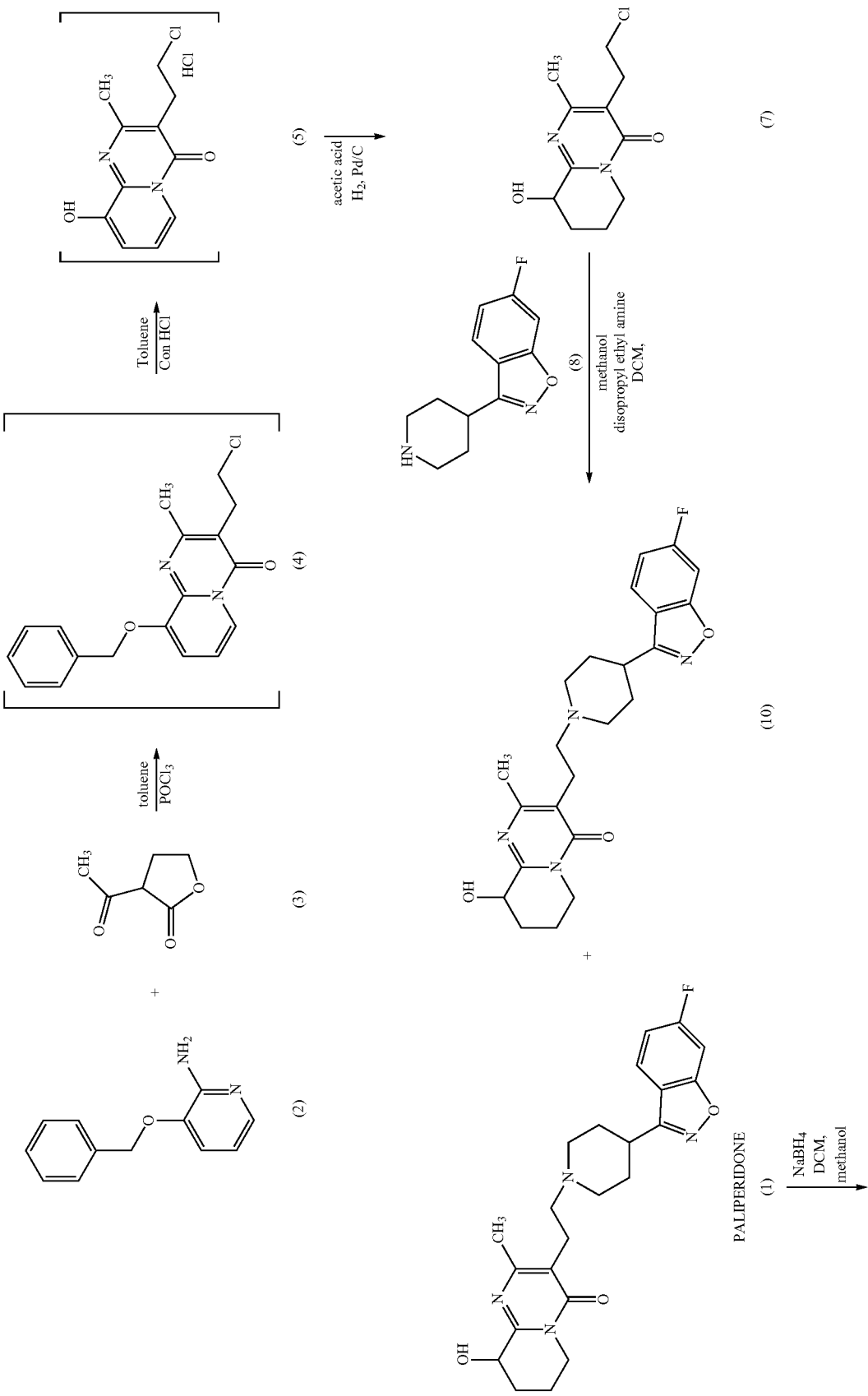

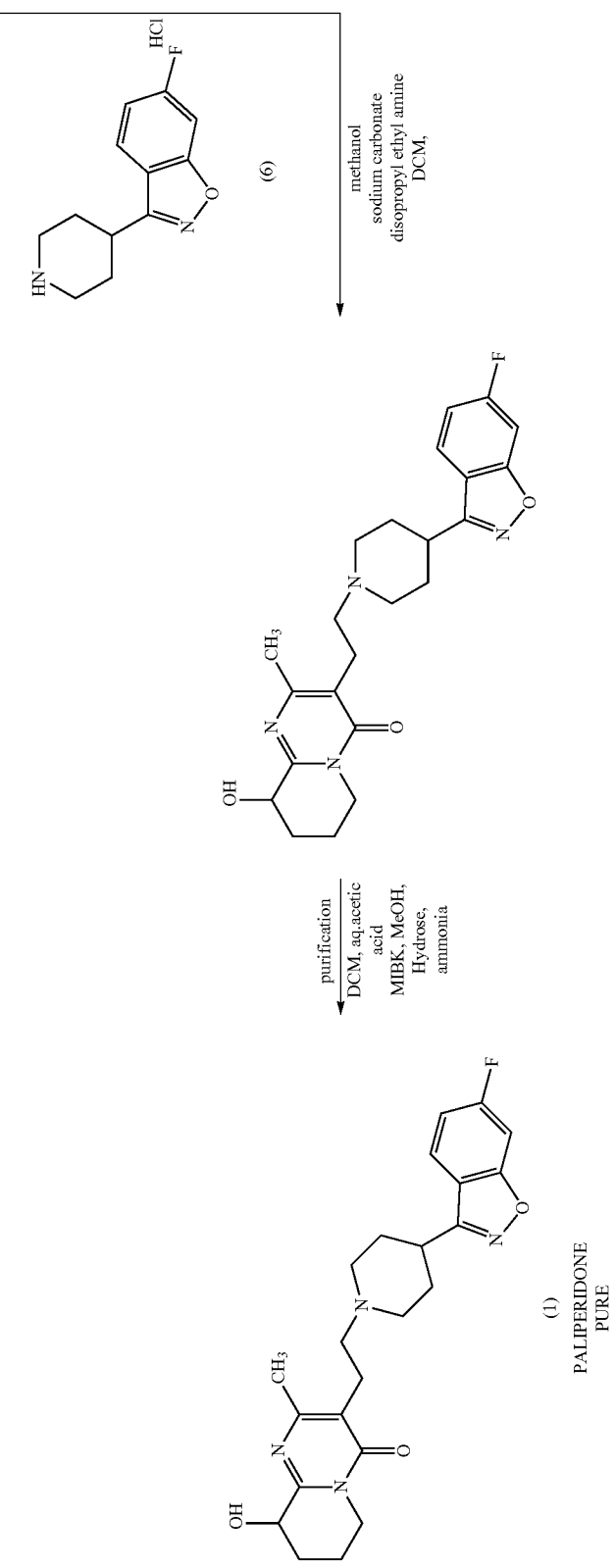

The third aspect of the present invention encompasses a novel process for the preparation of paliperidone compound of formula-1, which comprises of the following steps;
a) Reacting 3-(2-chloroethyl)-9-oxo-2-methyl-6,7,8,9-tetrahydro-4H-pyrido-[1,2-a]pyrimidin-4-one, compound of formula-9 with 6-fluoro-3-(4-piperidinyl)-1,2-benzisoxazole, crystalline solid compound of formula-8, in presence of a base in a suitable solvent, to provide 3-[2-[4-(6-fluoro-1,2-benzisoxazol-3-yl)piperidin-1-yl]ethyl]-9-oxo-2-methyl-6,7,8,9-tetrahydro-4H-pyrido-[1,2-a]pyrimidin-4-one, compound of formula-10,
b) treating the compound of formula-10 obtained in step a) with suitable reducing agent to obtain paliperidone,
c) purifying the crude paliperidone formed in step-b) by crystallizing it from alcohol, followed by treatment with acid, washing the aqueous layer with a suitable solvent and subsequent treatment with a base in presence of an alcohol to obtain pure paliperidone compound of formula-1.

The starting material 3-(2-chloroethyl)-9-oxo-2-methyl-6,7,8,9-tetrahydro-4H-pyrido-[1,2-a]pyrimidin-4-one, compound of formula-9 can be prepared by oxidizing 3-(2-chloroethyl)-9-hydroxy-2-methyl-6,7,8,9-tetrahydro-4H-pyrido-[1,2-a]pyrimidin-4-one, compound of formula-7 using oxalyl chloride in the presence of dimethyl sulfoxide.

In the step a) the base used for the condensation may be a suitable inorganic base or an organic base. The solvent used is selected without limitation, from either water or an aliphatic hydrocarbon or an aromatic hydrocarbon or a halogenated hydrocarbon or ether or a ketone or acetate or an alcohol or a nitrile.

In the step b) the 9-oxo group of 3-[2-[4-(6-fluoro-1,2-benzisoxazol-3-yl)piperidin-1-yl]ethyl]-9-oxo-2-methyl-6,7,8,9-tetrahydro-4H-pyrido-[1,2-a]pyrimidin-4-one, compound of formula-10, is reduced to hydroxy group using a suitable "reducing agent". The preferred reducing agent in the present embodiment is sodium borohydride.

In the step c) the paliperidone is recrystallised using alcohol solvent. The recrystallised product is subjected to treatment with an acid. Washed the obtained aqueous mass with a suitable solvent selected from ester solvent or ketone solvent to remove the impurities, followed by treatment with base in the presence or absence of alcohol solvent to obtain paliperidone of very high purity.

The present aspect of the invention is represented in Scheme-3.

The fourth embodiment of the present invention encompasses to a novel process for the preparation of paliperidone which comprises the following steps;
a) Reacting 3-(2-chloroethyl)-9-hydroxy-2-methyl-4H-pyrido-[1,2-a]pyrimidin-4-one hydrochloride compound of formula-5 with 6-fluoro-3-(4-piperidinyl)-1,2-benzisoxazole monohydrochloride, compound of formula-6 in presence of a base in suitable solvent, to provide 3-[2-[4-(6-fluoro-1,2-benzisoxazol-3-yl)piperidin-1-yl]ethyl]-9-hydroxy-2-methyl-4H-pyrido-[1,2-a]pyrimidin-4-one, compound of formula-11,
b) reducing compound of formula-11 by using a suitable reducing agent to obtain paliperidone,
c) purifying the crude paliperidone formed in step-b) by crystallizing it from isopropyl alcohol to obtain pure paliperidone compound of formula-1.

In the step-a, 3-(2-chloroethyl)-9-hydroxy-2-methyl-4H-pyrido-[1,2-a]pyrimidin-4-one hydrochloride is condensed with 6-fluoro-3-(4-piperidinyl)-1,2-benzisoxazole mono hydrochloride, compound of formula-6 in presence of a base in a suitable solvent, preferably sodium carbonate and catalytic amount of potassium iodide in acetonitrile, to provide 3-[2-[4-(6-fluoro-1,2-benzisoxazol-3-yl)piperidin-1-3/1]ethyl]-9-hydroxy-2-methyl-4H-pyrido-[1,2-a]pyrimidin-4-one, compound of formula-11. The reaction can be carried out in the presence or absence of a phase transfer catalyst.

In the U.S. Pat. No. 5,158,952 in the exemplified process the said condensation step is carried out in the presence of organic base i.e., diisopropyl amine to provide paliperidone. It also teaches that appropriate base such as for example, an alkali metal or alkaline metal carbonate, hydrogen carbonate, hydroxide, oxide, carboxylate, alkoxide hydride or amide e.g. sodium carbonate, sodium hydrogen carbonate, potassium carbonate, sodium hydroxide etc. can be used for the condensation. The reaction can be carried out in solvents such as aromatic solvents, $C_{1-6}$ alcohols, ketones, an ester, an ether, a dipolar aprotic solvent e.g. N,N-dimethyl formamide, N,N-dimethyl acetamide, dimethyl sulfoxide, pyridine, acetonitrile and the like; or a mixture of such solvents.

In the step-b, the pyridine ring of 3-[2-[4-(6-fluoro-1,2-benzisoxazol-3-yl)piperidin-1-yl]ethyl]-9-hydroxy-2-methyl-4H-pyrido-[1,2-a]pyrimidin-4-one, compound of formula-11, is reduced by a suitable reducing agent as defined earlier. Good yields were obtained on hydrogenation using palladium or platinum catalyst in acidic conditions. In the preferred embodiment the reaction was performed by hydrogenation using palladium catalyst in presence of acetic acid to provide pure paliperidone.

In the processes disclosed in the prior art the hydrogenation is performed in the presence of palladium catalyst in alcohol solvent, which to partially may lead to the hydrogenolysis of the chlorine atom which is replaced by hydrogen. The dehalogenated product does not undergo the condensation reaction in the next step, which leads to decrease in the purity and yields of the intermediates and it may be present as impurity. In the present invention the hydrogenation by palladium catalyst in acidic conditions prevents the dechlorination which leads to the increase in the purity and yield of the intermediates, and subsequently in the yield of the paliperidone.

The crude paliperidone formed in step-b, is purified by crystallizing from isopropyl alcohol to obtain pure paliperidone.

The present aspect of the invention is represented in Scheme-3 ence of N,N-dimethylformamide, sodium carbonate and catalytic amount of potassium iodide. The crude risperidone

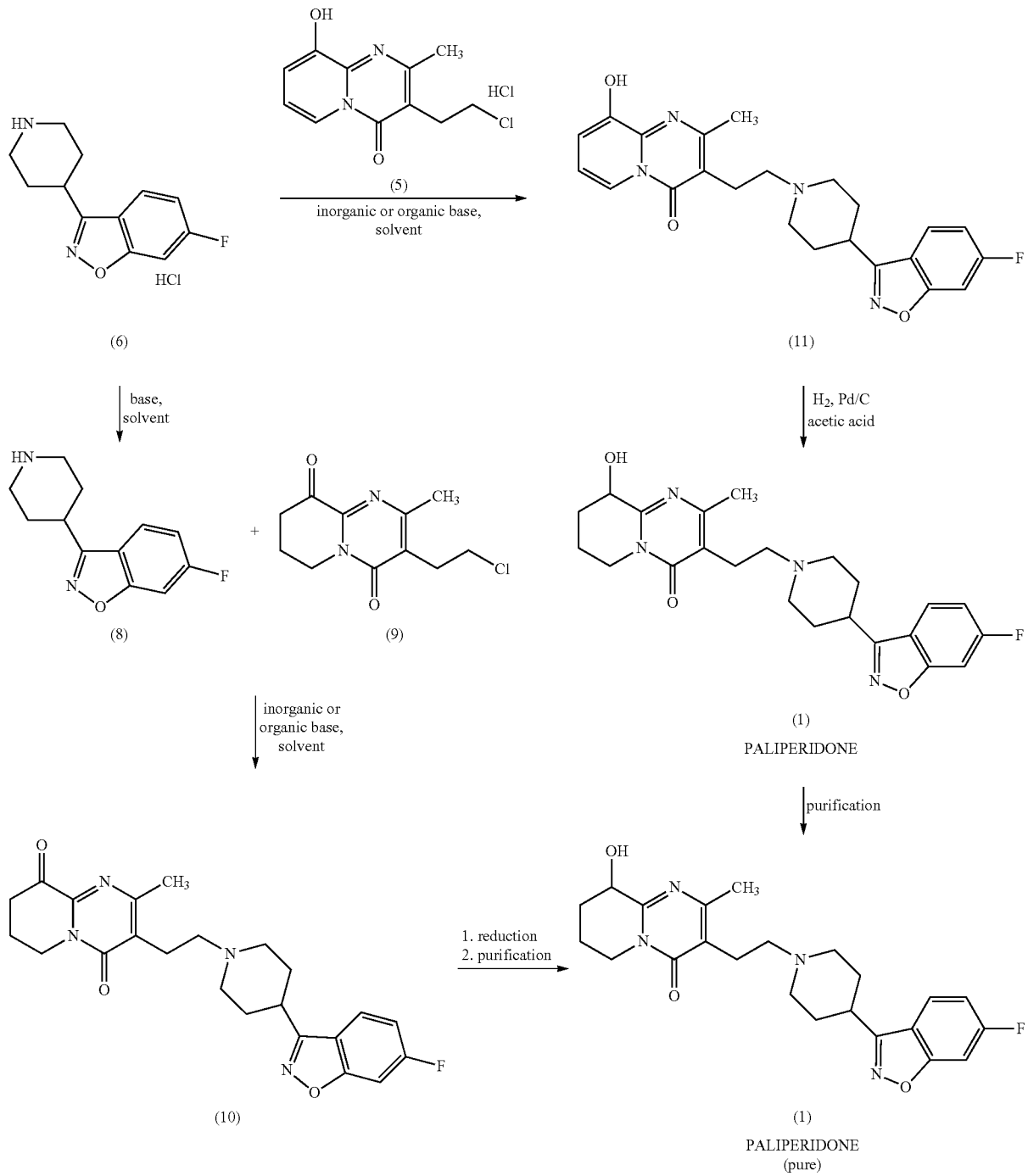

In the prior art above condensation step has been disclosed for the synthesis of analogous compounds especially risperidone and its analogues. U.S. Pat. No. 4,804,663 exemplifies the process for the preparation of risperidone, which includes the condensation of 3-(2-chloroethyl)-6,7,8,9-tetrahydro-2-methyl-4H-pyrido[1,2-a]pyrimidin-4-one and 6-fluoro-3-(4-piperidinyl)-1,2-benzisoxazole monohydrochloride in preswas crystallized from a mixture of DMF and isopropanol. A monograph in European pharmacopoeia on, risperidone, lists five impurities and paliperidone is one of them. Thus in the synthesis of paliperidone there is a possibility of formation of the similar impurities reported for risperidone.

The fifth aspect of the present invention encompasses a process for the preparation of crystalline 6-fluoro-3-(4-piperidinyl)-1,2-benzisoxazole, compound of formula-8, which comprises of the following steps;
a) treating 6-fluoro-3-(4-piperidinyl)-1,2-benzisoxazole monohydrochloride, compound of formula-6, with an aqueous base to convert it into its free base,
b) isolating the obtained solid from water or extracting the free base, compound of formula-8 from the reaction mixture, with a suitable solvent and concentrating the solvent to provide a crystalline solid compound of formula-8.

In the step a) of the present embodiment the salt of formula-6 is converted into its free base i.e. compound of formula-8, using aqueous base of alkali metal or alkaline metal carbonate, hydrogen carbonate, hydroxide.

In the step b) the free base is extracted from the reaction mixture using an aliphatic hydrocarbon or aromatic hydrocarbon or halogenated hydrocarbon or ester solvent.

The sixth aspect of the present invention encompasses crystalline form of 6-fluoro-3-(4-piperidinyl)-1,2-benzisoxazole.

Figure 2A:
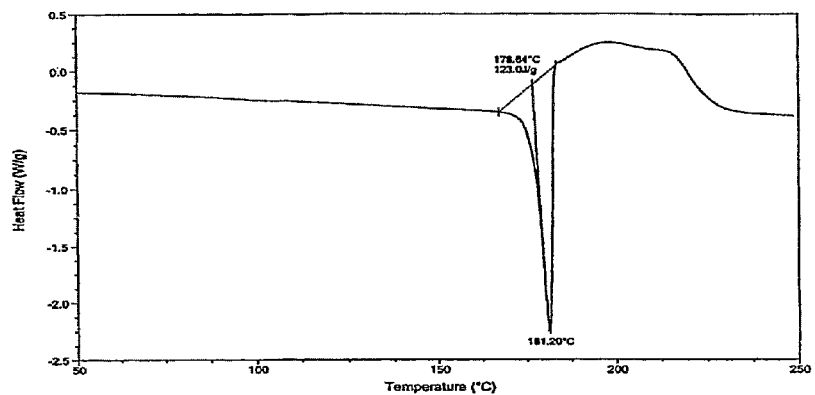
FIG. 2a: Illustrates the DSC of crystalline paliperidone.
Figure 2B:
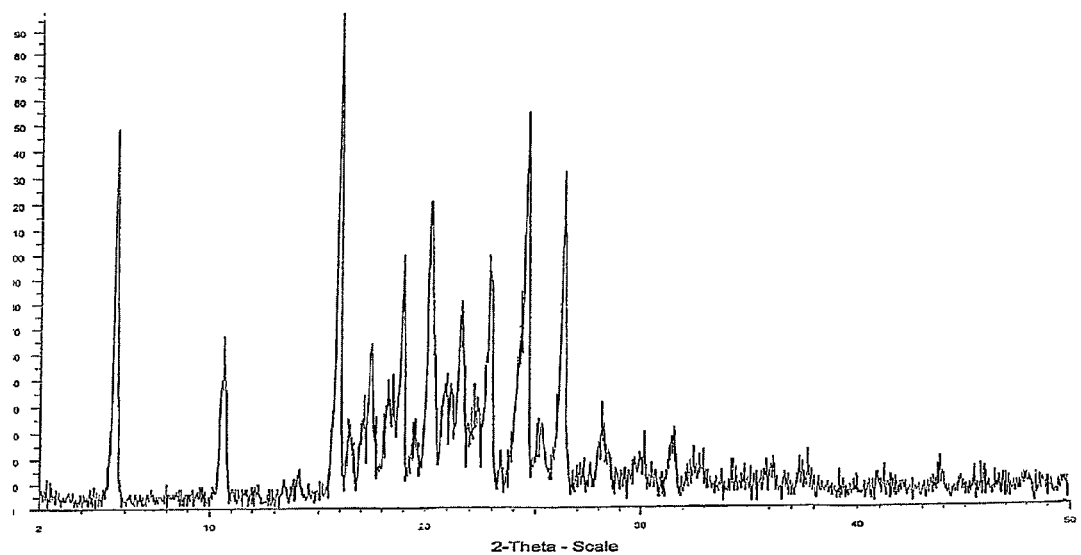
FIG. 2b: Illustrates the powder X-ray diffraction pattern of 6-fluoro-3-(4-piperidinyl)-1,2-benzisoxazole.

The crystalline 6-fluoro-3-(4-piperidinyl)-1,2-benzisoxazole, compound of formula-8 is characterized by its strong X-ray peaks at about 5.4, 10.5, 15.7, 17.3, 18.2, 18.8, 19.4, 20.1, 20.8, 21.5, 22.2, 22.8, 24.4, 26.2, 0.2 degrees two theta (as shown in FIG. 2b).

Figure 3A:
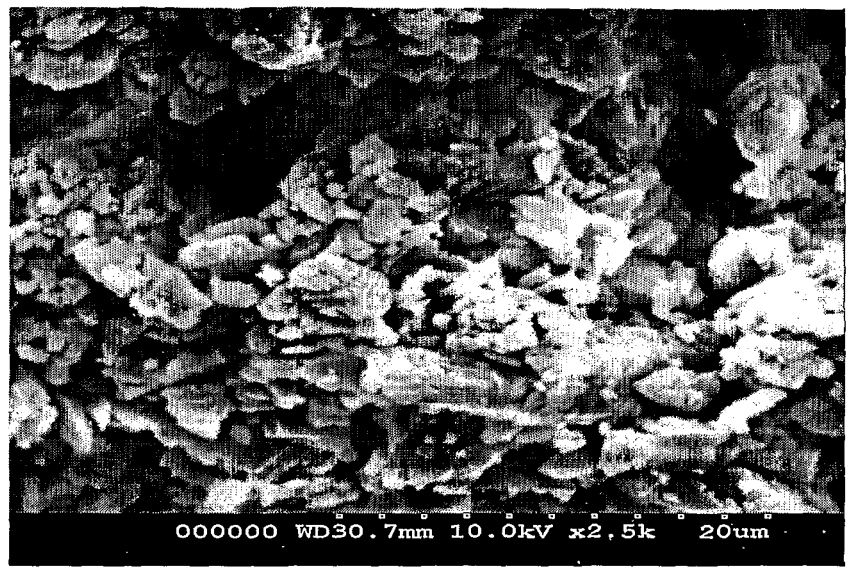
FIG. 3a: Illustrates the photograph of paliperidone as seen through a microscope.

The particles of paliperidone obtained as per the process of the present invention have porous texture and irregular shape morphology, when seen through the microscope (as shown in FIG. 3a). The porous nature of the particles may impart greater solubility to the drug substance.

Figure 3B:
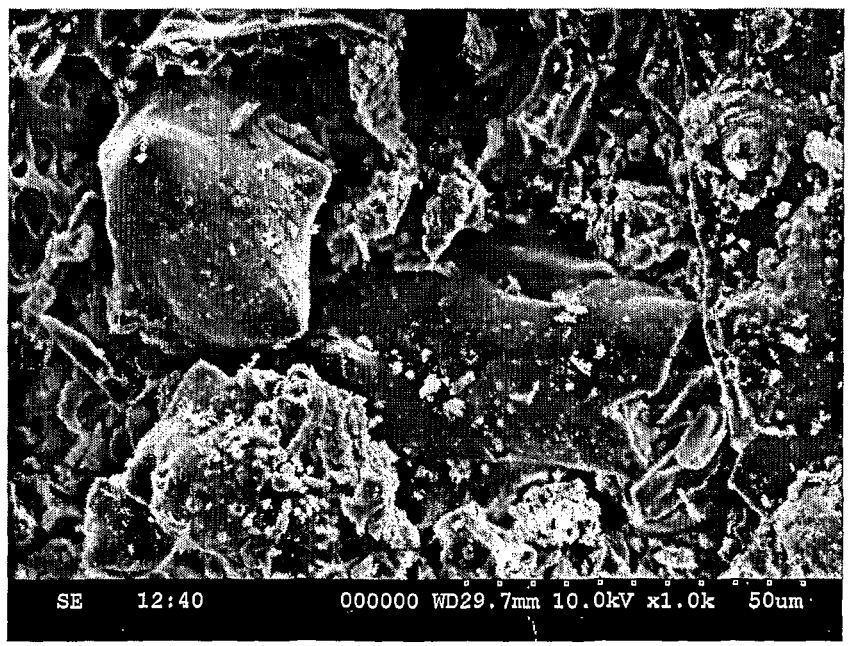
FIG. 3b: Illustrates the photograph of paliperidone obtained as per the prior art process as seen through the microscope

The particles of paliperidone prepared as per the process of the process disclosed in prior art (i.e., recrystallisation from isopropyl alcohol) have been obtained in the form of flakes with nonporous morphology, as seen through the microscope (FIG. 3b)

XRD analysis of crystalline 6-fluoro-3-(4-piperidinyl)-1,2-benzisoxazole was carried out using SIEMENS/D-5000 X-Ray diffractometer using Cu, Ka radiation of wavelength 1.54 A° and continuous scan speed of 0.045°/min.

Morphology of paliperidone was recorded as per the following method: The samples are moulded on alumina stubs using double adhesive tape, coated with gold using HUS-5 GB vacuum evaporator and observed in Hitachi S-520 Scanning Electron Microscope at an acculation voltage of 10 KV.

The related substance of paliperidone was analyzed by HPLC using the following conditions:
Column: ACE phenyl 250×4.6 mm; Flow rate: 10 µl ml/min; wavelength: 238 nm PDA; Temperature: 25° C.; Load: 10 µl; Run time: 45 min; and using acetonitrile and methanol in 1:1 ratio as a diluent.

The process described in the present invention was demonstrated in examples illustrated below. These examples are provided as illustration only and therefore should not be construed as limitation of the scope of the invention.

EXAMPLES

Example-1

Preparation of 3-(2-chloroethyl)-9-hydroxy-2-methyl-6,7,8,9-tetrahydro-4H-pyrido[1,2-a]pyrimidin-4-one. (formula-7)

To a solution of 2-Amino-3-benzyloxypyridine (formula-2) (20 grams) in toluene (40 ml) added 2-acetyl gammabutyro lactone (formula-3) (16.6 grams), stirred for 15 min and added phosphorus oxychloride (0.27 ml). The reaction mixture was refluxed for 12 hours and water was removed azeotropically. Then the reaction mixture was cooled to 70-80° C., added phosphorus oxychloride (11.9 ml) and then heated to 90-95° C. and stirred for 8 hr. The solvent was distilled off under reduced pressure and concentrated hydrochloric acid (70 ml) was added to the reaction mixture followed by toluene (100 ml) and stirred at 65-70° C. for 9 hours. The reaction mixture was cooled to 0-5° C. and the solid formed was filtered, washed with toluene and acetic acid. The wet solid was taken in autoclave along with acetic acid (110 ml), added Pd/C and applied 3.0-3.5 kg/cm² hydrogen pressure. The reaction mixture was heated to 50-60° C., stirred for 8 hrs, then cooled to 25° C. and quenched with water. The reaction mixture was filtered and the pH of the filtrate was adjusted to 11 using aqueous sodium hydroxide solution. Extracted the reaction mixture with ethyl acetate. The ethyl acetate layer was treated with basic carbon, filtered and distilled off under reduced pressure. The solid formed was taken in cyclohexane (45 ml) and stirred for 60 min at 25° C. The solid was filtered, washed with cyclohexane and dried to provide the title compound.

Yield: 11.0 grams.

Example-2

Preparation of Paliperidone

To a solution of 6-fluoro-3-(piperidin-4-yl)benzo[d]isoxazole HCl (formula-6) (20 grams) in methanol (100 ml) added sodium carbonate (12.7 g) and heated the mixture to 50-55° C. for 20-30 min. the reaction mixture was cooled to 35-40° C. and filtered. The filtrate was taken in a round bottomed flask and 3-(2-chloroethyl)-9-hydroxy-2-methyl-6,7,8,9-tetrahydro-4H-pyrido[1,2-a]pyrimidin-4-one (formula-7) (18.9 grams) was added to it followed by diisopropyl ethyl amine (15.5 grams). The reaction mixture was refluxed for 20-24 hours. The solvent was distilled off under reduced pressure; dichloromethane (600 ml) was added to the reaction mixture and stirred for 15-20 min. The reaction mixture was washed with aqueous sodium hydroxide solution (3×100 ml) followed by water at 20-25° C. The organic layer was separated and the solvent was distilled off under reduced pressure. Methanol (100 ml) was added to the reaction mixture and refluxed for 30-45 min. The reaction mixture was cooled to 20-25° C., stirred for one hour, filtered and washed with methanol to provide the title compound as a solid.

Yield: 22 grams.

Example 3

Preparation of Paliperidone

Step-A: To the solution of 6-fluoro-3-(piperidin-4-yl)benzo[d]isoxazole (formula-8) (5.0 grams) in methanol (25 ml) added 3-(2-chloroethyl)-9-hydroxy-2-methyl-6,7,8,9-tetrahydro-4H-pyrido[1,2-a]pyrimidin-4-one (formula-7) (5.5 grams) and diisopropyl ethylamine (4.5 grams). Heated the reaction mixture to reflux temperature and stirred for 20 hrs at same temperature. Cooled the reaction mixture to 20° C. and stirred for 90 minutes at the same temperature. Filtered the solid precipitated. Washed the solid with chilled methanol and dried the compound.

Yield: 6.9 grams.

Step-B: To the paliperidone obtained in step a) added dichloromethane (65 ml) and methanol (32.5 ml), stirred for 10 minutes and added sodium borohydride (0.03 g) to it. Stirred the reaction mixture for 90 minutes at 20° C. Distilled off the solvent completely under reduced pressure. Methanol (65 ml) was added to the reaction mixture and heated to reflux, cooled the reaction mixture to 20° C. and stirred for 90 minutes. Filtered the crystallized compound. Washed the compound with methanol and dried the compound to obtain paliperidone.

Yield: 5.5 grams.

Example-4

Preparation of Paliperidone 3-(2-chloroethyl)-9-hydroxy-2-methyl-6,7,8,9-tetrahydro-4H-pyrido[1,2-a]pyrimidin-4-one (formula-7) (5.2 grams) and diisopropyl ethyl amine (12.56 grams) was added to 6-fluoro-3-(piperidin-4-yl)benzo[d]isoxazole (formula-8) (5.0 grams) in methanol (75 ml) taken in autoclave and then heated to 60-65° C., 0.8 Kg pressure was applied and stirred for 16 hours. The reaction mixture cooled and then distilled under reduced pressure. Isopropyl alcohol was added to the obtained residue and stirred for 15 minutes and then distilled off under reduced pressure to get the title compound. Added methanol and heated the reaction mixture to reflux temperature and stirred for 2.0 hrs at same temperature. Cooled the reaction mixture to 20° C. and stirred for 90 minutes at the same temperature. Filtered the solid precipitated. Washed the solid with chilled methanol and dried the compound.

Yield: 3.0 grams.

Example-5

Preparation of 3-(2-chloroethyl)-9-hydroxy-2-methyl-6,7,8,9-tetrahydro-4H-pyrido[1,2-a]pyrimidin-4-one (formula-7)

A mixture of 3-(2-chloroethyl)-9-hydroxy-2-methyl-4H-pyrido[1,2-a]pyrimidin-4-one hydrochloride (formula-5) (40 grams), acetic acid (200 ml) and palladium carbon (40 grams) was taken in an autoclave. Hydrogen gas with a pressure of 3.0-3.5 Kg/cm$^2$ was applied to the above mixture at 35° C. for 6 hrs. The reaction was quenched with water and filtered the resultant mixture through a hyflow bed. The pH of the filtrate was adjusted to 6 using aqueous sodium hydroxide solution The reaction mixture was cooled to 0° C. and stirred for 1 hr. The solid formed was filtered, washed with water and dried to yield the title compound.

Yield: 22 grams.

Example-6

Preparation of Paliperidone (One Pot Process)

To the solution of 6-fluoro-3-(piperidin-4-yl)benzo[d]isoxazole (formula-8) (10.0 grams) in methanol (50 ml), 3-(2-chloroethyl)-9-hydroxy-2-methyl-6,7,8,9-tetrahydro-4H-pyrido[1,2-a]pyrimidin-4-one (formula-7) (11 grams) and diisopropyl ethyl amine (9 grams) were added. The reaction mixture heated to 65-70° C. and stirred for 24 hrs at the same temperature. The reaction mixture was cooled. Dichloromethane (100 ml) and sodium borohydride (0.086 grams) were added to it and stirred for 60 minutes at the same temperature. The solvent was distilled off under reduced temperature. Methanol was added to the residue and heated to reflux for 30 min. The reaction mixture was cooled to 20° C. and stirred for 1 hour. Filtered the solid precipitated. Washed the solid with chilled methanol and dried the compound.

Yield: 12.5 grams.

Example-7

Purification of Paliperidone

Paliperidone (25 grams) is suspended in dichloromethane 25 ml, stirred for 15 min and then aqueous acetic acid (12.5 ml of acetic acid dissolved in 50 ml water) was added and stirred for 15 min. The organic and aqueous layers were separated and the aqueous layer was washed with dichloromethane (12.5 ml) followed by methyl isobutyl ketone (25 ml) Hydrose (2.5 grams) was added to the aqueous layer and stirred for 10 min and then filtered. Added methanol (500 ml) to the filtrate. The pH of the mixture adjusted to 8-9 using ammonia solution and was stirred for 2 hrs at 35° C. and then cooled to 0-5° C. Filtered the solid obtained, washed with methanol and dried at 60° C. to provide pure paliperidone.

Yield: 18 grams.

PXRD of the obtained solid is shown in FIG. 1a.

Example-8

Preparation of 3-(2-chloroethyl)-9-oxo-2-methyl-6,7,8,9-tetrahydro-4H-pyrido[1,2-a]pyrimidin-4-one (formula-9)

A solution of oxalylchloride (8.8 ml) in dichloromethane (20 ml) was cooled to −65° C. and a solution of dimethyl sulfoxide (6.5 ml) dissolved in dichloromethane (20 ml) was added to it slowly and stirred for 30 min. keeping the temperature at −65° C. a solution of 3-(2-chloroethyl)-9-hydroxy-2-methyl-6,7,8,9-tetrahydro-4H-pyrido[1,2-a]pyrimidin-4-one (5 grams) (formula-7) dissolved in dichloromethane (30 ml) was added to it very slowly and stirred for 40 min. Triethyl amine was added to the reaction mixture and then quenched with water. The organic layer was separated, washed with aqueous sodium carbonate and water. The solvent from the organic layer was distilled off under reduced pressure to provide the title compound.

Yield: 4.0 grams

Example-9

Preparation of Paliperidone

Step-A: Preparation of 3-[2-[4-(6-fluoro-1,2-benzisoxazol-3-yl)piperidin-1-yl]ethyl]-9-oxo-2-methyl-6,7,8,9-tetrahydro-4H-pyrido-[1,2-a]pyrimidin-4-one (formula-10)

To the solution of 6-fluoro-3-(piperidin-4-yl)benzo[d]isoxazole (formula-8) (0.62 grams) taken in methanol added 3-(2-chloroethyl)-9-oxo-2-methyl-6,7,8,9-tetrahydro-4H-pyrido[1,2-a]pyrimidin-4-one (formula-9) (0.94 grams), diisopropyl ethyl amine (0.75 grams) and refluxed the reaction for 23 hrs. Cooled the reaction mixture to 26° C. and stirred for 15 minutes. Filtered the precipitated solid. Washed the solid with chilled methanol and dried. Separated the compound with column chromatography using chloroform/methanol as an eluent.

Yield: 0.3 grams

Step-B: Preparation of Paliperidone.

To a solution of 3-[2-[4-(6-fluoro-1,2-benzisoxazol-3-yl) piperidin-1-yl]ethyl]-9-oxo-2-methyl-6,7,8,9-tetrahydro-4H-pyrido-[1,2-a]pyrimidin-4-one (formula-10) (0.3 grams) taken in a mixture of methanol (1.5 ml) and dichloromethane (3 ml) added sodium borohydride (0.008 grams) and stirred for 1 hour at 30° C. The solvent was distilled off under reduced pressure. Methanol (1.5 ml) was added to it and heated to reflux for 30 min. the reaction mixture was cooled to 20° C. and stirred for 1 hour. Filtered the solid, washed with methanol and dried.

Yield: 0.2 grams.

Example-10

Preparation of 3-(2-chloroethyl)-9-hydroxy-2-methyl-4H-pyrido[1,2-a]pyrimidin-4-one hydrochloride (formula-5)

A mixture of 3-benzyloxy-2-aminopyridine (formula-2) (100 grams), toluene (3.5 L) and phosphorusoxychloride (139 ml) was heated to 50° C. 3-acetyldihydrofuran-2(3H)-2-one (218 grams) (formula-3) was added to the reaction mixture, heated to 95° C. and stirred for 18 hrs. The solvent was distilled off under reduced pressure to obtain a residue which was cooled to 40° C. and toluene (500 ml) was added to it. A solution of concentrated hydrochloric acid (600 ml) was added to the reaction mixture, heated to 60° C. and stirred for 6 hrs. The reaction mixture was cooled to 0° C. A solid crystallized out which was filtered, washed with toluene and dried at 50° C. to yield the title compound.

Yield: 95 grams.

Example-11

Preparation of 3-[2-[4-(6-fluoro-1,2-benzisoxazol-3-yl)piperidin-1-yl]ethyl]-9-hydroxy-2-methyl-4H-pyrido-[1,2-a]pyrimidin-4-one (formula-11)

A mixture of 3-(2-chloroethyl)-9-hydroxy-2-methyl-4H-pyrido[1,2-a]pyrimidin-4-one hydrochloride (formula-5) (11.1 grams), 6-fluoro-3-(4-piperidinyl)-1,2-benzoisoxazole mono hydrochloride (formula-6) (10 grams), sodium carbonate (7.5 grams), potassium iodide (0.64 grams) in acetonitrile (100 ml) was heated to 80-85° C. The reaction mixture was refluxed for 17 hrs under nitrogen. Then it was cooled to −10° C. and stirred for 30 min. The solid obtained was filtered and washed with chilled acetonitrile. The solid was taken in water and treated with sodiumhydrosulphite (hydrose) (2.0 grams). The solid was filtered and washed with water and dried at 50° C. to provide the title compound.

Yield: 12 grams.

Example-12

Preparation of Paliperidone

A mixture of 3-[2-[4-(6-fluoro-1,2-benzisoxazol-3-yl)piperidin-1-yl]ethyl]-9-hydroxy-2-methyl-4H-pyrido-[1,2-a]pyrimidin-4-one (formula-11) (5 grams), acetic acid (25 ml) and palladium carbon (4 grams) was taken in an autoclave. Hydrogen gas with a pressure of 3.0 Kg/cm$^2$ was applied to the above mixture at 32° C. for 9 hrs. The reaction mixture was filtered through a hyflow bed. The filtrate was treated with water (100 ml) and the pH of the filtrate was adjusted to 10 using aqueous sodium hydroxide solution. The solid formed was filtered, washed with water and dried at 50° C. to yield the title compound.

Yield: 1.7 grams.

Example-13

Preparation of Crystalline 6-fluoro-3-(4-piperidinyl)-1,2-benzisoxazole (formula-10): To the suspension of 6-fluoro-3-(piperidin-4-yl)benzo[d]isoxazole hydrochloride (25 grams) (formula-6) dissolved in water (100 ml), added aqueous sodium hydroxide (4.8 grams in 20 ml water). Stirred for 20 min and filtered the precipitated solid. Washed the solid with cold water and dried to obtain the title compound.

Yield: 19 grams.

Example-14

Preparation of Crystalline 6-fluoro-3-(4-piperidinyl)-1,2-benzisoxazole (formula-10)

To the suspension of 6-fluoro-3-(piperidin-4-yl)benzo[d]isoxazole hydrochloride (formula-6) (25 grams) dissolved in water (100 ml), added aqueous sodium hydroxide (4.8 g in 20 ml water). Stirred for 20 min and extracted with dichloromethane. Washed the organic layer with water, distilled off the solvent under reduced pressure to obtain the title compound.

Yield: 21 grams.

Example-15

Preparation of Paliperidone

A mixture of 3-(2-chloroethyl)-9-hydroxy-2-methyl-6,7,8,9-tetrahydro-4H-pyrido[1,2-a]pyrimidin-4-one (formula-8) (170.1 grams), 6-fluoro-3-(4-piperidinyl)-1,2-benzoisoxazole monohydrochloride (formula-6) (150 grams), sodium carbonate (113.3 grams), and potassium iodide (9.7 grams) in acetonitrile (1.5 L) was heated to 85° C. The reaction mixture was heated at 85° C. for 6 hrs. The reaction mixture was then cooled to −10° C. and stirred for 1.5 hrs. The solid obtained was filtered, washed with cold acetonitrile. The wet solid was taken in water, and acetic acid was added to the mixture to adjust the pH to 4.0. The reaction mixture was treated with acidic carbon and filtered through hyflow bed. The filtrate was treated with sodium hydrosulphite (hydrose). The pH of the reaction mixture was adjusted to 12 by adding aqueous sodium hydroxide solution and stirred for 45 min. The solid obtained was filtered, washed with water and dried to provide the title compound.

Yield: 224 grams.

Example-16

Purification of Paliperidone

The crude paliperidone (20 grams) obtained in example-3 was taken in isopropyl alcohol (1300 ml) and heated to reflux for 30 min. Basic carbon (10 grams) was added to the reaction mixture and refluxed further for 30 min. The reaction mixture was filtered through hyflow bed. The filtrate was cooled to 5° C. and stirred for 30 min. the solid obtained was filtered, washed with cold isopropyl alcohol and dried at 50° C. to provide pure paliperidone.

Yield: 16 grams.

Example-17

Purification of Paliperidone

Paliperidone (10 grams) was taken in isopropyl alcohol (650 ml) and heated the reaction mixture to 80-85° C. After getting clear solution it was cooled to 50° C. and neutral carbon (2 grams) was added to it. The reaction mixture was heated to 85° C. for 20 min and filtered through hyflow. The filtrate was cooled and filtered the precipitated solid. The wet solid was taken in water (50 ml) and acidified with acetic acid. Washed the reaction mixture with methyl isobutyl ketone and the aqueous layer was filtered. Hydrose (1 grams) and isopropyl alcohol (8 ml) were added to the filtrate and basified with ammonia solution. Stirred the reaction for 1 hr, filtered the solid precipitated and washed with water. Dried the solid to obtain pure paliperidone.

Yield: 7.6 grams (Purity by HPLC 99.60%).

Example-18

Purification of Paliperidone

Paliperidone (10 grams) was taken in isopropyl alcohol (650 ml) and heated the reaction mixture to 80-85° C. After getting clear solution it was cooled to 50° C. and neutral carbon (2 grams) was added to it. The reaction mixture was heated to 85° C. for 20 min and filtered through hyflow. The filtrate was cooled to 0° C. and filtered the precipitated solid. The wet solid was taken in water (50 ml) and acidified with acetic acid. Washed the reaction mixture with ethyl acetate and the aqueous layer was filtered. Hydrose (1 grams) and isopropyl alcohol (8 ml) were added to the filtrate and the reaction mixture was basified with ammonia solution. Stirred the reaction for 1 hr, filtered the solid precipitated and washed with water. Dried the solid to obtain pure paliperidone.

Yield: 8.0 grams (Purity by HPLC 99.90%).
Particle Size Distribution:
Before micronisation: D(0.1): 3.3 μm; D(0.5): 28.4 μm; D(0.9): 14.8 μm; D[4.3]: 46.02 μm.
After micronisation: D(0.1): 0.7 μm; D(0.5): 3.91 μm; D(0.9): 11.3 μm; D[4.3]: 5.4 μm Example-19

Purification of Paliperidone

Paliperidone (12 grams) was taken in isopropyl alcohol (780 ml) and heated the reaction mixture to 80-85° C. After getting clear solution it was cooled to 50° C. and neutral carbon (2.4 grams) was added to it. The reaction mixture was heated to 85° C. for 20 min and filtered through hyflow. The filtrate was cooled to 0° C. and filtered the precipitated solid. The wet solid was taken in water (120 ml) and acidified with acetic acid. Washed the reaction mixture with ethyl acetate followed by methyl isobutylketone and the aqueous layer were filtered. Hydrose (1.2 grams) and isopropyl alcohol (12 ml) were added to the filtrate and the basified with ammonia solution. Stirred the reaction for 1 hr, filtered the solid precipitated and washed with water. Dried the solid to obtain pure paliperidone.

Yield: 8.5 grams (Purity by HPLC 99.68%).

Example-20

Preparation of Prior Art Crystalline Form-I of Paliperidone

Paliperidone (25 grams) is suspended in dichloromethane 25 ml, stirred for 15 min and then aqueous acetic acid (12.5 ml of acetic acid dissolved in 50 ml water) was added and stirred for 15 min. The organic and aqueous layers were separated and the aqueous layer was washed with dichloromethane (12.5 ml) followed by methyl isobutyl ketone (25 ml) Hydrose (2.5 grams) was added to the aqueous layer and stirred for 10 min and then filtered. Added methanol (500 ml) to the filtrate. The pH of the mixture adjusted to 8-9 using ammonia solution and was stirred for 2 hrs at 35° C. and then cooled to 0-5° C. Filtered the solid obtained, washed with methanol and dried at 60° C. to provide pure paliperidone.

Yield: 16 grams.

PXRD diffractograms of the above obtained wet and dry solids are matching well with the PXRD of prior art crystalline form-I which is shown in FIG. 1a.

We claim:
1. A process for the preparation of paliperidone

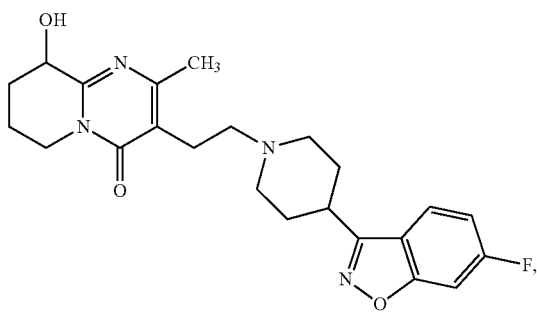

paliperidone the process comprising:
a) treating compound of formula-7

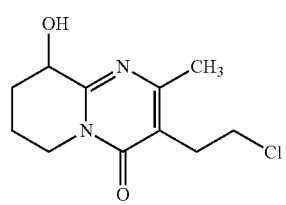

Formula-7 with crystalline solid compound of formula-8

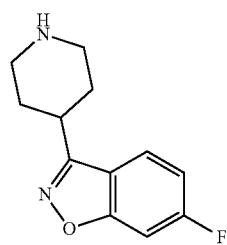

Formula-8 in presence of diisopropylethylamine in alcohol solvent to provide a mixture including paliperidone;

b) optionally, treating the mixture obtained in step a) with sodium borohydride to convert any amount of compound of formula-10

Formula-10

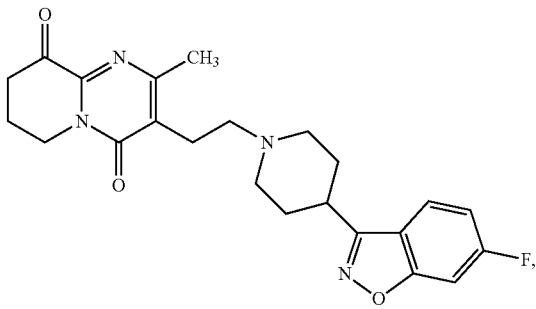

formed and present as an impurity, into paliperidone; and c) purifying the paliperidone obtained in step a) or step b) by suspending the paliperidone obtained in step a) or step b) in dichloromethane and treating the suspension with aqueous acetic acid to obtain a dichloromethane layer and an aqueous layer, separating the dichloromethane layer from the aqueous layer and washing the aqueous layer with methyl isobutyl ketone, treating the aqueous layer with hydrose, followed by basifying the aqueous layer with ammonia to provide purified paliperidone.

2. The process of claim 1, wherein step a) further comprises a) treating compound of formula-2

Formula-2 with compound of formula-3

Formula-3 in presence of phosphorus oxychloride in toluene to obtain compound of formula-4

Formula-4 which on treatment in-situ with an acid provides 3-(2-chloroethyl)-9-hydroxy-2-methyl-4H-pyrido-[1,2-a] pyrimidin-4-one, which is converted into its hydrochloride salt, a compound of formula-5

Formula-5 b) hydrogenating the compound of formula-5 in the presence of palladium catalyst under acidic conditions to obtain compound of formula-7

Formula-7 c) treating compound of formula-6

Formula-6 with sodium carbonate in methanol to obtain the crystalline solid compound of formula-8, then treating the crystalline solid compound of formula-8 with the compound of formula-7 in presence of diisopropylethylamine in methanol to obtain paliperidone.

3. The process of claim 2, wherein the acid in step a) is selected from the group consisting of hydrochloric acid, hydrobromic acid and sulfuric acid, and combinations thereof.

4. The process of claim 2, wherein the acid in step a) is hydrochloric acid.

5. The process of claim 2, wherein the acid in step a) is hydrobromic acid.

6. The process of claim 2, wherein the compound of formula-5 is hydrogenated in the presence of the palladium catalyst and acetic acid.

7. The process of claim 1, wherein step a) further comprises:

a) treating compound of formula-6

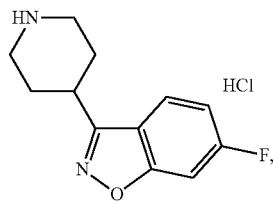

Formula-6 with an aqueous base to convert the compound of formula-6 into the compound of formula-8; and b) isolating the compound of formula-8 from water, or extracting the compound of formula-8 from the reaction mixture with a solvent and removing the solvent to provide the compound of formula-8 as a crystalline solid.

8. The process of claim 1, wherein the crystalline solid compound of formula-8 is characterized by X ray peaks at about 5.4, 10.5, 15.7, 17.3, 18.2, 18.8, 19.4, 20.1, 20.8, 21.5, 22.2, 22.8, 24.4, and 26.2, ±0.2 degrees two theta.

9. The process of claim 1, wherein the paliperidone obtained in step a) is treated with sodium borohydride in methanol.

10. The process of claim 1, wherein step c) further comprises basifying the aqueous layer with ammonia in the presence of methanol to obtain the purified paliperidone.

* * * * *